US012605351B2

(12) United States Patent
Andre et al.

(10) Patent No.: US 12,605,351 B2
(45) Date of Patent: Apr. 21, 2026

(54) METHOD FOR PRODUCING A COMPOSITION COMPRISING A 3-O-p-COUMAROYL ESTER OF TORMENTIC ACID FROM A PLANT CELL CULTURE, APPLICATIONS THEREOF AS ANTIPARASITIC AGENT FOR THE TREATMENT OF TRYPANOSOMIASIS

(71) Applicants: LUXEMBOURG INSTITUTE OF SCIENCE AND TECHNOLOGY, Esch-sur-Alzette (LU); Université catholique de Louvain, Ottignies-Louvain-la-Neuve (BE)

(72) Inventors: Christelle Andre, Hondelange (BE); Joelle Leclercq, Beaufays (BE); Claire Beaufay, Etterbeek (BE); Lucy Catteau, Woluwe-Saint-Lambert (BE); Sylvain Legay, Metz (FR)

(73) Assignee: LUXEMBOURG INSTITUTE OF SCIENCE AND TECHNOLOGY, Esch-sur-alzette (LU)

( * ) Notice: Subject to any disclaimer, the term of this patent is extended or adjusted under 35 U.S.C. 154(b) by 944 days.

(21) Appl. No.: 17/428,369

(22) PCT Filed: Feb. 6, 2020

(86) PCT No.: PCT/EP2020/052952
§ 371 (c)(1),
(2) Date: Aug. 4, 2021

(87) PCT Pub. No.: WO2020/161221
PCT Pub. Date: Aug. 13, 2020

(65) Prior Publication Data

US 2022/0151970 A1 May 19, 2022

(30) Foreign Application Priority Data

Feb. 7, 2019 (LU) ........................................ 101117

(51) Int. Cl.

| | |
|---|---|
| ***A61K 31/215*** | (2006.01) |
| ***A01H 4/00*** | (2006.01) |
| ***A61K 31/19*** | (2006.01) |
| ***A61P 33/02*** | (2006.01) |
| ***C12P 15/00*** | (2006.01) |

(52) U.S. Cl.
CPC ........... *A61K 31/215* (2013.01); *A01H 4/005* (2013.01); *A61K 31/19* (2013.01); *A61P 33/02* (2018.01); *C12P 15/00* (2013.01); *A61K 2236/00* (2013.01)

(58) Field of Classification Search
CPC .. A61K 31/215; A61K 31/19; A61K 2236/00; A01H 4/005; A61P 33/02; C12P 15/00
See application file for complete search history.

(56) References Cited

U.S. PATENT DOCUMENTS

| | | | | |
|---|---|---|---|---|
| 2005/0255569 A1 | | 11/2005 | Matsuyama et al. | |
| 2010/0159545 A1* | | 6/2010 | Kim | C12N 5/04 435/146 |
| 2010/0317606 A1 | | 12/2010 | Chan et al. | |
| 2019/0134128 A1 | | 5/2019 | Nguyen et al. | |

FOREIGN PATENT DOCUMENTS

| | | |
|---|---|---|
| JP | 2011026265 | 2/2011 |

OTHER PUBLICATIONS

Li, Junqiang, et al. "Embryogenesis and Plant Regeneration from Anther Culture in Loquat (Eriobotrya Japonica L.)." Scientia Horticulturae, vol. 115, No. 4, Feb. 2008, pp. 329-336. ScienceDirect, https://doi.org/10.1016/j.scienta.2007.10.007. (Year: 2007).*
Verardo, Giancarlo, et al. "High Triterpenic Acids Production in Callus Cultures from Fruit Pulp of Two Apple Varieties." Phytochemical Analysis: PCA, vol. 28, No. 1, Jan. 2017, pp. 5-15. PubMed, https://doi.org/10.1002/pca.2638. (Year: 2017).*
He, Qian-Qian, et al. "Chemical Constituents of Gold-red Apple and Their α-Glucosidase Inhibitory Activities." Journal of Food Science, vol. 79, No. 10, Oct. 2014. DOI.org (Crossref), https://doi.org/10.1111/1750-3841.12599. (Year: 2014).*
Xu, Xuan, et al. "Harnessing Apple Cell Suspension Cultures in Bioreactors for Triterpene Production: Transcriptomic Insights into Biomass and Triterpene Biosynthesis." International Journal of Molecular Sciences, vol. 26, No. 7, Mar. 2025, p. 3188. (Year: 2025).*

(Continued)

*Primary Examiner* — Clinton A Brooks
*Assistant Examiner* — Kyle Nottingham
(74) *Attorney, Agent, or Firm* — IPSILON USA, LLP

(57) ABSTRACT

The present invention relates to a method for the production of a (poly)hydroxylated pentacyclic triterpene composition including a 3-O-p-coumaroyl ester of tormentic acid from a plant suspension cell culture, to a pharmaceutical composition comprising at least 3-O-p-coumaroyl ester of tormentic acid for a use in the prevention and/or the treatment of trypanosomiasis, optionally in admixture with other (poly) hydroxylated pentacyclic triterpenes, and to 3-O-p-coumaroyl ester of tormentic acid for its use as an antiparasitic agent for the prevention and/or the treatment of trypanosomiasis, optionally in admixture with other (poly)hydroxylated pentacyclic triterpenes.

16 Claims, 2 Drawing Sheets

(56) References Cited

OTHER PUBLICATIONS

Taniguchi Shoko et al: "Production of bioactive triterpenes by Eriobotrya japonicacalli" Phytochemistry, Pergamon Press, GB, vol. 59, No. 3, May 9, 2017, pp. 315-323.
Sylvian Cretton et al: "Chemical constituents from Waltheria indica exert in vitro activity against Trypanosoma prucei and T. cruzi" vol. 105, Jun. 11, 2015, pp. 55-60.
Daniele Da Silva Ferreira et al: "In activity of ursolic and oleanolic acids during the acute phase of Trypanosoma cruzi infection" Experimental Parasitology, vol. 134, No. 4, Mar. 3, 2013.
Kiangj I U He et al: "Triterpenoids Isolated from Apple Peels Have Potent Antiproliferative Activity and May Be Partially Responsible for Apple's Anticancer Activity" Journal of Agricultural and Food Chemistry, May 1, 2007.
International Search Report dated Mar. 3, 2020.
Search Report dated Jul. 1, 2019.

* cited by examiner

METHOD FOR PRODUCING A COMPOSITION COMPRISING A 3-O-p-COUMAROYL ESTER OF TORMENTIC ACID FROM A PLANT CELL CULTURE, APPLICATIONS THEREOF AS ANTIPARASITIC AGENT FOR THE TREATMENT OF TRYPANOSOMIASIS

RELATED APPLICATION

This application is a National Phase of PCT/EP2020/052952 filed on Feb. 6, 2020, which claims the benefit of priority from Luxembourg Patent Application No. 10 1117, filed on Feb. 7, 2019, the entirety of which are incorporated by reference.

FIELD OF THE INVENTION

The present invention belongs to the field of production of bioactive compounds, particularly for pharmaceutical applications.

More precisely, the present invention relates to a method for the production of a (poly)hydroxylated pentacyclic triterpene composition including a 3-O-p-coumaroyl ester of tormentic acid from a plant suspension cell culture, to a pharmaceutical composition comprising at least 3-O-p-coumaroyl ester of tormentic acid for a use in the prevention and/or the treatment of trypanosomiasis, optionally in admixture with other (poly)hydroxylated pentacyclic triterpenes, and to 3-O-p-coumaroyl ester of tormentic acid for its use as an antiparasitic agent for the prevention and/or the treatment of trypanosomiasis, optionally in admixture with other (poly)hydroxylated pentacyclic triterpenes.

DESCRIPTION OF RELATED ART

Infectious diseases, such as malaria, leishmaniasis and trypanosomiasis, remain to this day one of the major public health problems that concern an important part of the world with high economic and mortality impact. Despite some improvements, the situation is still alarming: according to the 2014 WHO report (WHO, 2014, World Health Statistics 2014, Geneva), infectious diseases cause life expectancy to decrease by 8% in high-income countries and by 70% in the African region.

Trypanosomiasis may lead, according to the parasitic species involved, to Chagas disease also known as American Trypanosomiasis (*Trypanosoma cruzi*) or to sleeping sickness also known as Human African Trypanosomiasis (*Trypanosoma brucei*), which cause important health problems and may be lethal if untreated. More than 10 000 persons die every year due to Chagas disease complications with about 8 million people affected worldwide. For the African infection, 61 million people are at risk in 36 countries. However, control efforts achieve to decrease by 100-times each year death reported cases, with 3000 in 2015. Progress has to be sustained and new therapeutic agents are still needed, especially with oral route and safe efficiency on second-stage infection (WHO 2018), (Urbina, J. A., Journal of Eukaryotic Microbiology, 2015, 62(1) 149-56).

Sleeping sickness is notoriously difficult to treat considering the toxicity and complex administration of the drugs currently available for treatment. Furthermore, parasite resistance to existing drugs is always a risk. Only four drugs are registered for the treatment of human African trypanosomiasis: pentamidine, suramin, melarsoprol and eflornithine. A fifth drug, nifurtimox, is used in combination under special authorizations. Fexinidazole recently obtained a positive opinion by the Committee for Medicinal Products for Human Use (CHMP) of the European Medicine Agency (EMA) but is only effective for some forms of the illness (those due to *Trypanosoma brucei gambiense*) [EMA site consulted 20-12-2018]. However, none of them are anodyne as all have a certain level of toxicity (WHO web site consulted 20-12-2018).

The goals of therapy in persons with *T. cruzi* infection are to eliminate the parasites with specific drug treatment and to manage the signs and symptoms that result from the largely irreversible lesions associated with the disease. In 2017, benznidazole was approved by the FDA for the treatment of Chagas disease caused by *T. cruzi* in children aged 2-12 years. Nifurtimox is available through the CDC Drug Service for specific treatment of *T. cruzi* infection. For the most part, both benznidazole and nifurtimox are limited in their capacity to effect parasitological cure, especially in chronically infected patients. Moreover, it has not been established in properly structured trials that treatment of chronically infected persons with either benznidazole or nifurtimox improves outcomes (Louis V Kirchhoff, MedScape, September 2018).

Thus, the use of these drugs in such patients continues to be controversial.

Therefore, research on a safer, more effective, affordable and shorter-course treatment is urgent in the fight of these two forms of trypanosomiasis.

In this context, natural compounds are a prime target for the development of new active hits. Indeed, nature has already provided a large source of new molecules and new skeletons. A special focus is made on pentacyclic triterpenes, C30 terpenes consisting of six isoprene units. In human, they possess numerous biomedical properties, including anti-inflammatory (Andre, C. M. et al., Journal of Agricultural and Food Chemistry, 2012, 60, 10546-10554), anti-cancer (Salvador, J. A. et al., Natural Product Reports, 2012, 29, 1463-1479), and anti-plasmodial activities (Bero, J. et al., Journal of Pharmacy and Pharmacology, 2009, 61, 1401-1433). They may also serve as scaffolds for the semi-synthesis of new lead bioactive agents. Triterpenes are distinguished by their remarkable structural diversity, with more than 20,000 different triterpenes reported to date (Hill, R. A. and Connolly, J. D., Natural Product Reports, 2013, 30, 1028-1065). As a consequence, a wide array of biological properties has also been described. Triterpene esters for instance, such as triterpene-hydroxycinnamates are of particular interest as they have been reported in some cases with increased anti-inflammatory, anti-malarial and anti-cancer activities as compared to their non-esterified counterparts (Suksamrarn, S. et al., Chemical and Pharmaceutical Bulletin, 2006, 54, 535-537; Ma, C. Y. et al., Chemistry & Biodiversity, 2008, 5, 2442-2448; Kikushi, T., et al., Journal of Natural Products, 2011, 74, 137-144; WO2007/145253).

Polyhydroxylated triterpenes such as tormentic acid have also been associated with numerous health benefits such as lipid-lowering (WO2013/171100) and anti-neoplasic activities (WO2004/030682), and as pharmaceutical agent in the treatment of ischemic heart diseases (WO2007/048353).

Concerning their antiparasitic activities, a recent review reported the high activity of 85 pentacyclic triterpenes against different species of *Plasmodium, Trypanosoma, Leishmania* and *Nematoda* highlighting the great interest for this phytochemical group (Isah M. B. et al., Parasitology, 2016, 143, 1219-1231). According to this review, tingenin, a quinone methide, is the most active reported pentacyclic triterpene against *Trypanosoma brucei brucei* and *Trypano-*

*soma cruzi* with $IC_{50}<0.25$ μg/mL against both species. However, with other compounds belonging to the same class, this compound has been found highly cytotoxic on MCR-5 cells ($IC_{50}=0.45$ μg/mL—Maregesi, S. M. et al., Journal of Ethnopharmacology, 2010, 129(3), 319-326).

In addition, efficient processes for their production are still missing, which is an essential prerequisite for their pharmaceutical interest and commercial deployment. Most current methodologies are based on extracting as starting material whole plants or agro-wastes that are potentially pesticide-contaminated, along with low extraction rates regarding the most biologically active triterpenes. Furthermore, pollutant solvents such as ethyl acetate or hexane, are commonly proposed as extracting solvent (WO2011/147028).

Objects and Summary

Therefore, the inventors have set themselves to provide a more effective, safer and highly selective anti-trypanosomial treatment together with an easy process for its production starting from a plant material.

Further to intensive researches, the inventors have found that a specific ester of tormentic acid, namely 3-O-p-coumaroyl ester of tormentic acid (trans- and/or cis-forms), or a (poly)hydroxylated pentacyclic triterpenes composition including 3-O-p-coumaroyl ester of tormentic acid, in admixture with tormentic acid, maslinic acid, annurcoic acid, and corosolic acid, exhibits a strong selective antitrypanosomal activity in vitro with $IC_{50}=0.76\pm0.31$ μg/mL (Selectivity Index (SI)=92 compared to cytotoxicity in Human fibroblast Cell line WI38, with $IC_{50}=80.40\pm5.56$ μg/mL). In addition, an in vivo antitrypanosomal study shows that this compound has no acute toxicity at a total cumulative dose of 100 mg/kg, and that the treatment of infected mice treated intraperitoneally with this ester at 50 mg/kg/d during five days (day 3-7 post-infection with $10^4$ Tbb/mouse) led to a significant decrease in the parasitemia at day 4 post-infection as well as a significant increase in mice survival compared to vehicle treated mice.

3-O-p-coumaroyl ester of tormentic acid has already been described for other therapeutic properties such as for example as anti-fungal (CN105104394), as anti-bacterial, bone loss-related disease-improving agent (JP2015/178480), etc, but never as antitrypanosomal agent.

In addition, the Inventors have found that this particular ester can be easily produced from a plant material, with a good yield, and preferably without using any harmful or toxic compounds.

A first object of the present invention is therefore a method for producing, from a plant cell suspension culture, a composition comprising a mixture of (poly)hydroxylated pentacyclic triterpenes including at least a 3-O-p-coumaroyl ester of tormentic acid and/or a derivative thereof, wherein said method comprises at least the following steps:

1) providing a suspension-cultured cell line capable of producing a mixture of (poly)hydroxylated pentacyclic triterpenes including at least a 3-O-p-coumaroyl ester of tormentic acid and/or a derivative thereof, said suspension-cultured cell line being cultured in a liquid culture medium from a callus of a plant selected in the group of Rosaceae and Sapotaceae families;
2) adding in said liquid culture medium at least one elicitor and culturing the suspension-cultured cell line of step 1) in said liquid culture medium during a period of time sufficient to produce said mixture of (poly)hydroxylated pentacyclic triterpenes including at least a 3-O-p-coumaroyl ester of tormentic acid and/or a derivative thereof;
3) extracting said mixture of (poly)hydroxylated pentacyclic triterpenes including at least a 3-O-p-coumaroyl ester of tormentic acid and/or a derivative thereof from the liquid culture medium with a solvent, to obtain a first composition comprising said mixture of (poly)hydroxylated pentacyclic triterpenes including a first concentration C1 of a 3-O-p-coumaroyl ester of tormentic acid and/or a derivative thereof in said solvent,
4) submitting the first composition of step 3) to a silica gel chromatography to obtain a second composition comprising a mixture of (poly)hydroxylated pentacyclic triterpenes including a second concentration C2 of said 3-O-p-coumaroyl ester of tormentic acid and/or a derivative thereof, with C2 being higher than C1.

Thanks to this method, it is now possible to access easily, from a plant material, with a good yield, and without using any harmful or toxic compounds, to a specific (poly)hydroxylated pentacyclic triterpenes composition including at least a 3-O-p-coumaroyl ester of tormentic acid (also known as 3β-trans/cis-p-coumaroyl-2α,19α-dihydroxy-urs-12-en-28-oic acid) and/or a derivative thereof, such composition exhibiting a high anti-trypanosomal activity. In addition, this method is industrially-scalable using stirred-tank bioreactors. A high yield of triterpenes is obtained (up to 83.5 mg of triterpenes per gram of dry cell weight have been isolated) by implementing the method according to the present invention. Finally, the culture of plant callus is performed in vitro, under sterile and controlled condition. This is a great advantage for the pharmaceutical industry. Moreover, as the plant calluses are originating from the Rosaceae family or from the Sapotaceae family, the worldwide availability of those raw materials can be exploited.

The 3-O-p-coumaroyl ester of tormentic acid has two isomeric forms, i.e. 3-O-trans-p-coumaroyl ester of tormentic acid and 3-O-cis-p-coumaroyl ester of tormentic acid, which are respectively represented by formula ($1_t$) et ($1_c$) below:

($I_t$)

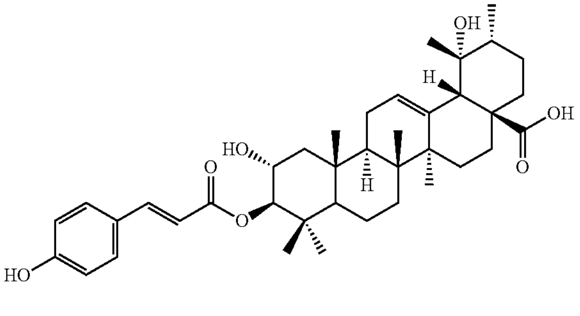

-continued ($I_c$)

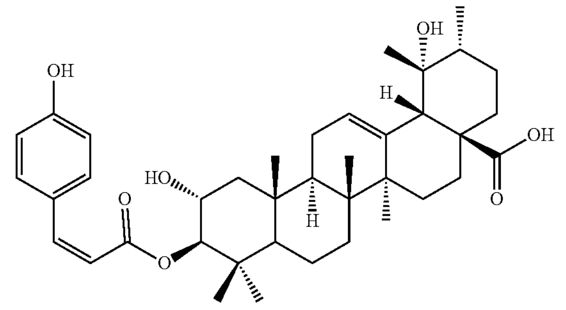

According to the present invention, a derivative of 3-O-p-coumaroyl ester of tormentic acid is a compound of formula ($I_t$) or ($I_c$) in which at least one double bond may be absent and in which at least one of the free hydroxyl functions is esterified and/or at least one of the methyl groups and/or at least one of the hydroxyl groups and/or at least one hydrogen are replaced with another substituent, and/or bearing at least one substituent on at least one carbon of the rings constituting the acid skeleton. As an example, a derivative of 3-O-p-coumaroyl ester of tormentic acid can be represented by formula (II) below:

(II)

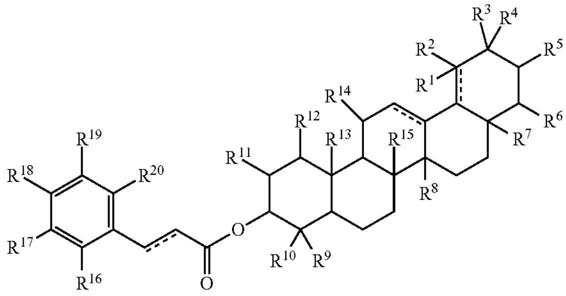

wherein

- $R^1$ to $R^{15}$ are each individually selected in the group consisting of H, OH, O-alkyl, alkyl, =O, $CH_2OH$, COOH and COO-alkyl;
- $R^{16}$ to $R^{20}$, are each individually selected in the group consisting of H, OH, O-alkyl, alkyl, =O, $CH_2OH$, COOH and X, wherein X=F, Cl or Br;
- the bond represented by a continuous line doubled with a dotted line corresponds either to a single bond or a double bond.

The alkyl and O-alkyl radicals preferably have from 1 to 5 carbon atoms.

According to a preferred embodiment of the present invention, derivatives of formula (II) are selected in the group of compounds in which:

- $R^1$ to $R^6$ and $R^8$ to $R^{15}$ are each individually selected in the group consisting of H, hydroxyl, and a methyl radical,
- $R^7$ is COOH,
- $R^{16}$ to $R^{20}$, are each individually selected in the group consisting of H, hydroxyl, and X, with X=F, Cl or Br.

Among derivatives of formula (II), one can particularly mention derivatives of formulae (II-1) to (II-10) below:

(II-1)

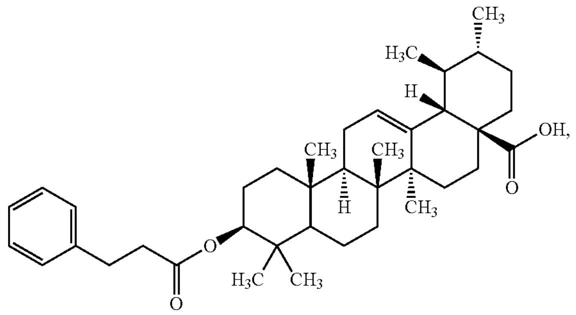

named 3-O-hydrocinnamic ursolic acid (II-2)

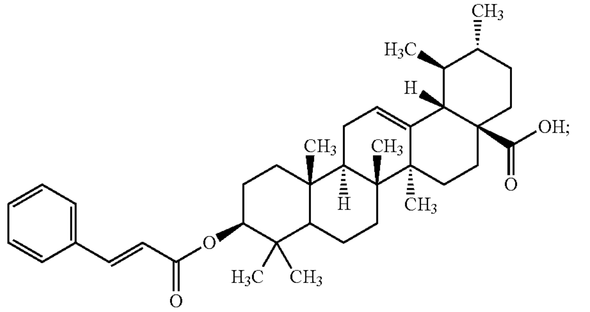

named 3-O-cinnamic ursolic acid (II-3)

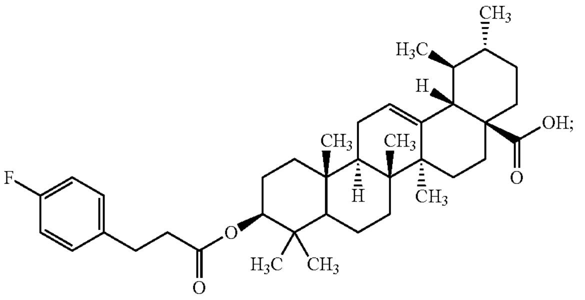

named 3-O-parafluorophenylpropionic ursolic acid (II-4)

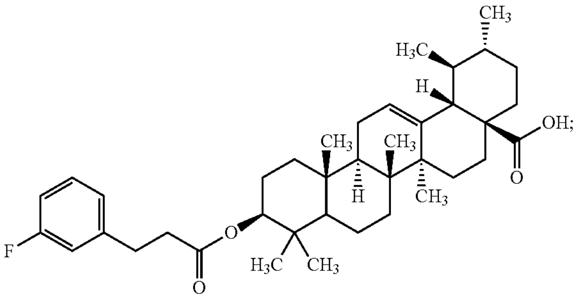

named 3-O-orthofluorophenylpropionic ursolic acid

-continued (II-5)

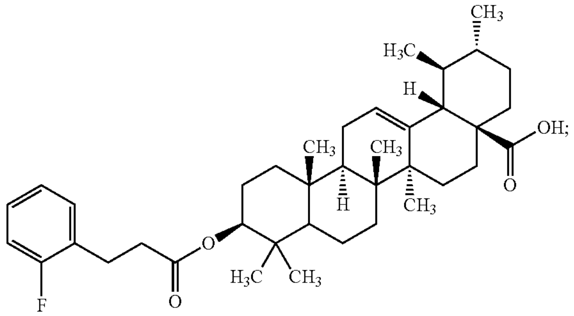

named 3-O-metafluorophenylpropionic ursolic acid (II-6)

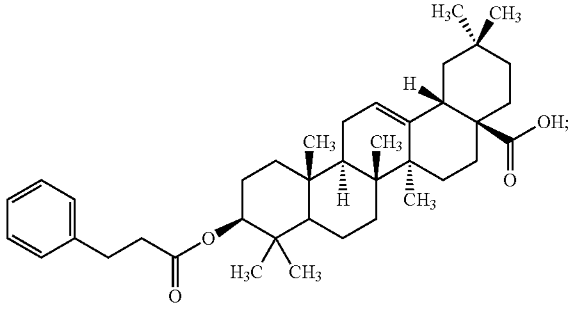

named 3-O-hydrocinnamic oleanolic acid (II-7)

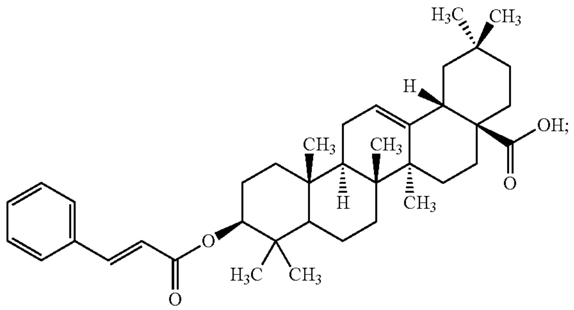

named 3-O-cinnamic oleanolic acid (II-8)

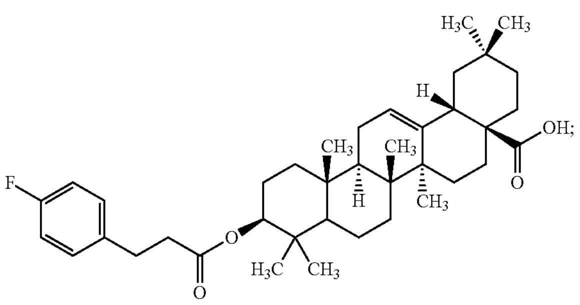

named 3-O-parafluorophenylpropionic oleanolic acid

-continued (II-9)

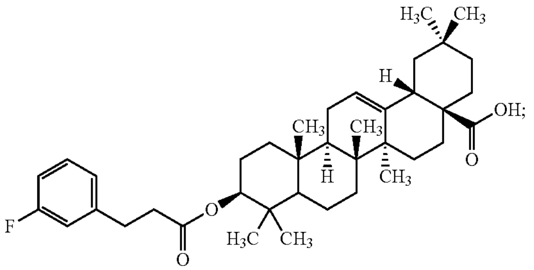

and named 3-O-metafluorophenylpropionic oleanolic acid (II-10)

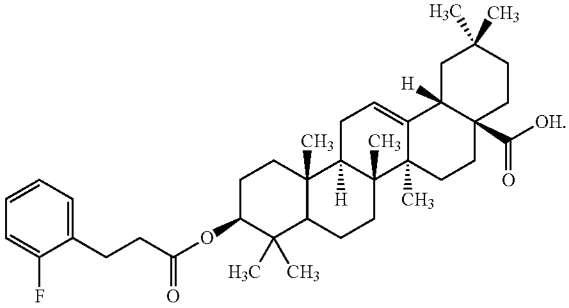

named 3-O-orthofluorophenylpropionic oleanolic acid

Derivatives of 3-O-p-coumaroyl ester of tormentic acid, and in particular derivatives of formula (II), may be prepared starting from 3-O-p-coumaroyl ester of tormentic acid or other triterpenes as obtained according to the method of the present invention, after isolation of the compound of interest. For example, hydroxyl function at position 3 from the oleanolic and ursolic acids template can be targeted to synthetize cinnamic esters following the Steglich esterification.

Preferably, the callus used to prepare the suspension-cultured cell line of step 1) is obtained from the fruits when the plant belongs to the Rosaceae family or from the leaves when the plant belongs to the Sapotaceae family.

According to a preferred embodiment of the present invention, the callus used to prepare the suspension-cultured cell line of step 1) is a callus obtained from a fruit of the Rosaceae family, more preferably from fruits of apples (species *Malus* x *domestica*, in particular *Malus* x *domestica* Borkh.) and pears (Genus *Pyrus*). Among apples and pears, apples are particularly preferred.

According to the invention, the plant of the group of the Rosaceae family is selected in the group comprising the species *Malus* x *domestica* (apple tree), in particular *Malus* x *domestica* Borkh., and the plant of the group of Sapotaceae is selected in the group comprising the species *Vitellaria paradoxa* C. F. Gärtn., commonly known as shea tree, shi tree or *Vitellaria.*

According to a preferred embodiment of the present invention, the callus is a *Malus* x *domestica* Borkh. Cultivar, including "Cox's Orange Pippin", "Spartan" and "Golden Delicious" cultivars, the "Cox's Orange Pippin" cultivar being particularly preferred.

During step 2), an elicitor is used to activate the pathway of the secondary metabolism and enhance the production of the target (poly)hydroxylated triterpenes, in particular the production of 3-O-p-coumaroyl ester of tormentic acid.

The elicitor used in step 2) of the method according to the invention can be an abiotic elicitor such as a stress plant hormone or a metal or a biotic elicitor such as a yeast extract.

Among stress plant hormones, one can for example mention abscisic acid, auxins, brassinosteroids, cytokinins, ethylene, gibberellins, salicylic acid, strigolactones and jasmonates such as in particular methyl jasmonate.

When a metal is used as elicitor, said metal can be chosen among copper, silver, cadmium, manganese, nickel, vanadium, etc., preferably in the forms of a salt.

According to a particular and preferred embodiment of the present invention, the elicitor used during step 2) is a stress plant hormone, more preferably a jasmonate derivative, and even more preferably methyl jasmonate.

The amount of elicitor added in the liquid culture medium used during step 2) may range from about 10 μM to 150 μM, preferably from about 50 μM to 100 μM.

The liquid culture medium used during step 2), preferably comprises a sugar as a carbon source and at least one additional plant hormone in the auxin family, preferably 1-naphtaleneacetic acid and/or 2,4-dichlorophenoxyacetic acid.

According to a preferred embodiment of the present invention, the liquid culture medium used during step 2) is a Linsmaier and Skoog medium further comprising sucrose as carbon source, and 1-naphtaleneacetic acid and 2,4-dichlorophenoxyacetic acid as auxin derivatives. Linsmaier and Skoog medium is a culture medium well known in the art, containing macroelements such as ammonium nitrate, calcium chloride, magnesium sulphate, potassium nitrate, potassium phosphate monobasic; microelements such as boric acid, cobalt chloride hexa hydrate, copper sulphate pentahydrate, EDTA disodium salt dihydrate, ferrous sulphate heptahydrate, manganese sulphate monohydrate, molybdic acid (sodium salt), potassium iodide, zinc sulphate heptahydrate; and vitamins such as myo-inositol and thiamine hydrochloride.

The amount of added sucrose in such a medium may vary from about 28 to 50 g/L, and more preferably from 29 to 35 g/L.

1-naphtaleneacetic acid and 2,4-dichlorophenoxyacetic acid are preferably added into the liquid culture medium used during step 2) each in a same amount which may vary from about 0.1 to 0.5 to 0.5 mg/L. According to a particularly preferred embodiment of the present invention, each of 1-naphtaleneacetic acid and 2,4-dichlorophenoxyacetic acid is present in the liquid culture medium in an amount of about 0.20 mg/L.

Step 2) is preferably carried out at a temperature ranging from about 20 to 25° C., during a period of time ranging from about 1 week to 4 weeks, preferably from about 3 weeks to 4 weeks.

The solvent used during step 3) can be chosen among ethyl acetate, hexane, n-butanol, dichloromethane, ethanol, methanol, acetone, etc. . . . , and mixtures thereof. Preferably, this solvent is a food grade solvent, more preferably ethanol.

According to a preferred embodiment of the present invention, ultrasonic waves (sonication) can be applied to the mixture of the liquid culture medium with a solvent during step 3) to enhance the extraction of (poly)hydroxylated pentacyclic triterpenes from the liquid culture medium towards the solvent. Preferably, sonication can be performed at a power of 200 to 2000 W, for about 5 to 20 min.

After sonication, the mixture is preferably maintained under mechanical agitation, for 1 to 10 hours, preferably at a temperature ranging from about 4 to 20° C.

The mixture of (poly)hydroxylated pentacyclic triterpenes present in the first composition obtained at the end step 3) comprises 3-O-trans-p-coumaroyltormentic acid and/or 3-O-cis-p-coumaroyltormentic acid and at least one pentacyclic triterpene compound preferably selected in the group comprising tormentic acid, maslinic acid, annurcoic acid and corosolic acid.

In the first composition obtained at the end of step 3), 3-O-p-coumaroyl ester of tormentic acid and/or a derivative thereof may be the major pentacyclic triterpene component. That means that the concentration C1 of a 3-O-p-coumaroyl ester of tormentic acid and/or a derivative thereof is higher than the individual concentrations of each other pentacyclic triterpenic components that are present in said first composition. The amount C1 of 3-O-trans-p-coumaroyltormentic acid and/or of 3-O-cis-p-coumaroyltormentic acid and/or a derivative thereof is of at least 1 weight % with regards to the total extract weight.

According to a particular embodiment of the present invention, and when the callus used in step 1) is obtained from a plant of Rosaceae family, in particular *Malus* x *domestica*, then the mixture of (poly)hydroxylated pentacyclic triterpenes of the first composition obtained at the end of step 3) comprises 3-O-trans-p-coumaroyltormentic acid and/or 3-O-cis-p-coumaroyltormentic acid, tormentic acid, maslinic acid, annurcoic acid and corosolic acid.

At the end of step 4), the second composition preferably comprises a concentration C2 of 3-O-trans-p-coumaroyltormentic acid and/or of 3-O-cis-p-coumaroyltormentic acid of at least about 10 weight % with regards to the total weight of the mixture of (poly)hydroxylated pentacyclic triterpenes present in said second composition.

In the second composition obtained at the end of step 4), 3-O-p-coumaroyl ester of tormentic acid and/or a derivative thereof may be the major pentacyclic triterpene component. That means that the concentration C2 of a 3-O-p-coumaroyl ester of tormentic acid and/or a derivative thereof is higher than the individual concentrations of each other pentacyclic triterpene components that are present in said second composition.

According to a particular embodiment of the present invention, and when the callus used in step 1) is obtained from a plant of Rosaceae family, in particular *Malus* x *domestica*, then the mixture of (poly)hydroxylated pentacyclic triterpenes of the second composition obtained at the end of step 4) comprises from about 10 to 33 weight % of 3-O-trans-p-coumaroyltormentic acid, from about 1 to 6 weight % of 3-O-cis-p-coumaroyltormentic acid, from about 6 to 20 weight % of tormentic acid, from about 9 to 21 weight % of maslinic acid, from about 7 to 32 weight % of annurcoic acid and from about 5 to 12 weight % of corosolic acid, with regards to the total weight of the mixture of (poly)hydroxylated pentacyclic triterpenes present in said composition.

Always according to this particular embodiment, a most preferred mixture of (poly)hydroxylated pentacyclic triterpenes of the second composition obtained at the end of step 4) preferably comprises:

i) about 26 weight % of 3-O-trans-p-coumaroyltormentic acid, about 4 weight % of 3-O-cis-p-coumaroyltormentic acid, about 20 weight % of tormentic acid, about 16 weight % of maslinic acid, about 12 weight % of annurcoic acid and about 9 weight % of corosolic acid; or ii) about 16 weight % of 3-O-trans-p-coumaroyltormentic acid, about 5 weight % of 3-O-cis-p-coumaroyltormentic acid, about 11 weight % of tormentic acid, about 21 weight % of maslinic acid, about 31 weight % of annurcoic acid and about 12 weight % of corosolic acid, or iii) about 33 weight % of 3-O-trans-p-coumaroyltormentic acid, about 1.5 weight % of 3-O-cis-p-coumaroyltormentic acid, about 8 weight % of tormentic acid, about 29 weight % of annurcoic acid, about 13.5 weight % of maslinic acid, and about 7.5 weight % of corosolic acid.

According to another embodiment of the present invention, and when the callus used in step 1) is obtained from a plant of Sapotaceae family, in particular *Vitellaria paradoxa*, then the mixture of (poly)hydroxylated pentacyclic triterpenes of the second composition obtained at the end of step 4) comprises from about 4 to 10 weight % of 3-O-trans-p-coumaroyltormentic acid, from about 0 to 2 weight % of 3-O-cis-p-coumaroyltormentic acid, from about 34 to 43 weight % of tormentic acid, from about 10 to 16 weight % of maslinic acid, from about 11 to 14 weight % of corosolic acid, from about 2 to 6 weight % of oleanolic acid, from about 8 to 12 weight % of ursolic acid, and from 12 to 17 weight % of oxidosqualene, with regards to the total weight of the mixture of (poly)hydroxylated pentacyclic triterpenes present in said composition.

The silica gel chromatography of the first composition during step 4) may be carried out on a silica gel cartridge, for example in a column packed with $C_{18}$ silica gel particles having a diameter ranging from about 40 to 63 μm in suspension in a solvent, preferably a food grade solvent such as ethanol or a mixture of ethanol and water. Elution can be performed with an appropriate solvent, such as for example mixtures of ethanol and water in different volume ratios.

At the end of step 4), the method according to the present invention may further comprise an additional step 5) of isolating said 3-O-p-coumaroyl ester of tormentic acid from the second composition obtained at the end of step 4), in order to obtain a third composition containing only 3-O-trans-p-coumaroyltormentic acid and/or 3-O-cis-p-coumaroyltormentic acid.

The isolation of step 5) can be performed by preparative chromatography, in particular by High Pressure Liquid Chromatography (HPLC), coupled to an UV detector and using, as mobile phase, a mixture of solvents (e.g., water, acetonitrile and/or methanol). Identification and quantification of triterpenic compounds collected in the different fractions can thereafter be performed by Ultra Performance Liquid Chromatography (UPLC) coupled to a diode array detector (DAD), hyphenated with a high-resolution mass spectrometer (Triple TOF).

The composition comprising mixture of (poly)hydroxylated pentacyclic triterpenes including at least a 3-O-p-coumaroyl ester of tormentic acid and/or a derivative thereof obtained at the end of step 4) of the method according to the present invention is novel as such and constitutes a second object of the present invention.

A second object of the present invention is thus a composition comprising a mixture of (poly)hydroxylated pentacyclic triterpenes including at least a 3-O-p-coumaroyl ester of tormentic acid and/or a derivative thereof, wherein said composition may be obtained by the method defined in anyone of claims 1 to 16, and wherein the mixture of (poly)hydroxylated pentacyclic triterpene comprises 3-O-trans-p-coumaroyltormentic acid and/or 3-O-cis-p-coumaroyltormentic acid and at least one triterpenic compound selected in the group comprising tormentic acid, tormentic acid, maslinic acid, annurcoic acid and corosolic acid.

The advantage of using this composition is that it is technically much easier and cheaper to produce in larger scale than a pure compound while its efficiency against trypanosomiasis is nevertheless very good.

The concentration C2 of 3-O-trans-p-coumaroyltormentic acid and/or 3-O-cis-p-coumaroyltormentic acid is of at least about 10 weight % with regards to the total weight of the mixture of (poly)hydroxylated pentacyclic triterpenes present in said composition.

According to a particular and preferred embodiment of the second object of the present invention, this composition is directly obtained by the method defined as the first object of the present invention in which the callus used in step 1) is obtained from a plant of Rosaceae family, in particular *Malus* x *domestica*, then said composition comprises from about 10 to 33 weight % of 3-O-trans-p-coumaroyltormentic acid, from about 1 to 6 weight % of 3-O-cis-p-coumaroyltormentic acid, from about 6 to 20 weight % of tormentic acid, from about 9 to 21 weight % of maslinic acid, from about 7 to 32 weight % of annurcoic acid and from about 5 to 12 weight % of corosolic acid with regards to the total weight of the mixture of (poly)hydroxylated pentacyclic triterpenes present in said composition.

Always according to this particular embodiment of the second object of the present invention, a most preferred mixture of (poly)hydroxylated pentacyclic triterpenes of said composition comprises:

i) about 26 weight % of 3-O-trans-p-coumaroyltormentic acid, about 4 weight % of 3-O-cis-p-coumaroyltormentic acid, about 20 weight % of tormentic acid, about 16% weight % of maslinic acid, about 12 weight % of annurcoic acid and about 9 weight % of corosolic acid; or ii) about 16 weight % of 3-O-trans-p-coumaroyltormentic acid, about 5 weight % of 3-O-cis-p-coumaroyltormentic acid, about 11 weight % of tormentic acid, about 21 weight % of maslinic acid, about 31 weight % of annurcoic acid and about 12 weight % of corosolic acid.

As demonstrated in the following examples, 3-O-trans-p-coumaroyltormentic acid and 3-O-cis-p-coumaroyltormentic acid, alone or in admixture with other (poly)hydroxylated pentacyclic triterpene compounds such as tormentic acid, maslinic acid, annurcoic acid and/or corosolic acid, have a strong selective anti-trypanosomal activity and can therefore be used as antiparasitic agents for the prevention and/or the treatment of trypanosomiasis. In particular, the results shown in these examples demonstrate that for 3-O-cis/trans-p-coumaroyltormentic acid, this activity is 10 times higher than that of tormentic acid.

A third object of the present invention is therefore a 3-O-p-coumaroyl ester of tormentic acid and/or a derivative thereof for a use as a drug for the prevention and/or the treatment of trypanosomiasis.

Preferably, the 3-O-p-coumaroyl ester of tormentic acid is 3-O-trans-p-coumaroyltormentic acid and/or 3-O-cis-p-coumaroyltormentic acid.

Finally, a fourth object of the present invention is a pharmaceutical composition comprising, as an active principle, a 3-O-p-coumaroyl ester of tormentic acid and/or a derivative thereof and at least one pharmaceutically acceptable excipient for a use in the prevention and/or the treatment of trypanosomiasis.

Preferably said pharmaceutical composition comprises at least 3-O-trans-p-coumaroyltormentic acid and/or 3-O-cis-p-coumaroyltormentic acid.

Such a composition may further comprise at least one additional pentacyclic triterpenic compound preferably selected in the group comprising tormentic acid, maslinic acid, annurcoic acid and corosolic acid.

According to an embodiment of the fourth object of the present invention, the pharmaceutical composition comprises a mixture of (poly)hydroxylated pentacyclic triterpenes comprising from about 10 to 33 weight % of 3-O-trans-p-coumaroyltormentic acid, from about 1 to 6 weight % of 3-O-cis-p-coumaroyltormentic acid, from about 6 to 20 weight % of tormentic acid, from about 9 to 21 weight % of maslinic acid, from about 7 to 32 weight % of annurcoic acid and from about 5 to 12 weight % of corosolic acid with regards to the total weight of the mixture of (poly)hydroxylated pentacyclic triterpenes present in said composition.

According to another embodiment of the fourth object of the present invention, the pharmaceutical composition comprises about 26 weight % of 3-O-trans-p-coumaroyltormentic acid, about 4 weight % of 3-O-cis-p-coumaroyltormentic acid, about 20 weight % of tormentic acid, about 16% weight % of maslinic acid, about 12 weight % of annurcoic acid and about 9 weight % of corosolic acid.

According to another embodiment of the fourth object of the present invention, the pharmaceutical composition comprises about 16 weight % of 3-O-trans-p-coumaroyltormentic acid, about 5 weight % of 3-O-cis-p-coumaroyltormentic acid, about 11 weight % of tormentic acid, about 21 weight % of maslinic acid, about 31 weight % of annurcoic acid and about 12 weight % of corosolic acid.

The pharmaceutical composition of the present invention may be administered by any suitable route, for example, by oral, buccal, inhalation, sublingual, nasal, percutaneous, i.e., transdermal, or parenteral (including intravenous, intramuscular, subcutaneous and intracoronary) administration. Therefore, the pharmaceutical composition of the invention can be provided in various forms, such as in the form of hard gelatin capsules, of capsules, of compressed tablets, of suspensions to be taken orally, of lozenges or of injectable solutions or in any other form appropriate to the method of administration.

According to a preferred embodiment of the invention, the pharmaceutical composition is for a parenteral administration.

The pharmaceutical composition according to the invention includes those wherein the 3-O-p-coumaroyl ester of tormentic acid and/or a derivative thereof is administered in an effective amount to achieve its intended purpose. Determination of the effective amounts is well within the capability of those skilled in the art.

The exact formulation, route of administration, and dosage can be chosen by the individual physician in view of the patient's conditions. Dosage amount and interval of administration can be adjusted individually to provide plasma levels of the 3-O-p-coumaroyl ester of tormentic acid and/or a derivative thereof which are sufficient to maintain the preventive or therapeutic effects.

The amount of pharmaceutical composition administered will therefore depend on the subject being treated, on the subject's weight, the severity of the affliction and the manner of administration.

For human use, the 3-O-p-coumaroyl ester of tormentic acid and/or a derivative thereof can be administered alone, but they are preferably administered in admixture with at least one pharmaceutically acceptable carrier, the nature of which will depend on the intended route of administration and the presentation form. Pharmaceutical composition for use according to the present invention thus can be formulated in a conventional manner using one or more physiologically acceptable carriers comprising one or more excipients and auxiliaries that facilitate processing of the 3-O-p-coumaroyl ester of tormentic acid and/or a derivative thereof into preparations which can be used pharmaceutically. Amongst the excipients and auxiliaries which can be used in the pharmaceutical composition according to the invention, one can mention anti-agglomerating agents, anti-oxidants, preservative agents, dyes, vitamins, inorganic salts, taste-modifying agents, smoothing agents, coating agents, isolating agents, stabilizing agents, wetting agents, anti-caking agents, dispersing agents, emulsifying agents, aromas, penetrating agents, solubilizing agents, etc. . . . , mixtures thereof and generally any excipient conventionally used in the pharmaceutical industry.

For general information about the formulation and administration of pharmaceutical compositions, one can obviously refer to the book "Remington's Pharmaceutical Sciences", last edition. Of course, a person skilled in the art will take care on this occasion that the excipient(s) and/or auxiliary (ies) optionally used are compatible with the intrinsic properties attached to the pharmaceutical composition in accordance with the invention.

These pharmaceutical compositions can be manufactured in a conventional manner, e.g., by conventional mixing, dissolving, granulating, dragee-making, emulsifying, encapsulating, entrapping, or lyophilizing processes. Proper formulation is dependent upon the route of administration chosen.

BRIEF DESCRIPTION OF DRAWINGS

Besides the arrangements above, the invention also comprises other arrangements which will emerge from the following description, which refers to examples of preparation of a mixture of (poly)hydroxylated pentacyclic triterpenes comprising 3-O-cis/trans-p-coumaroyltormentic acid according to the invention, to in vitro demonstration of the anti-trypanosomial activity of 3-O-cis/trans-p-coumaroyltormentic acid and to in vivo demonstration of the anti-trypanosomial activity of 3-O-cis/trans-p-coumaroyltormentic acid and also to the annexed FIGS. 1 to 3 in which.

DETAILED DESCRIPTION

Examples

Figure 1:
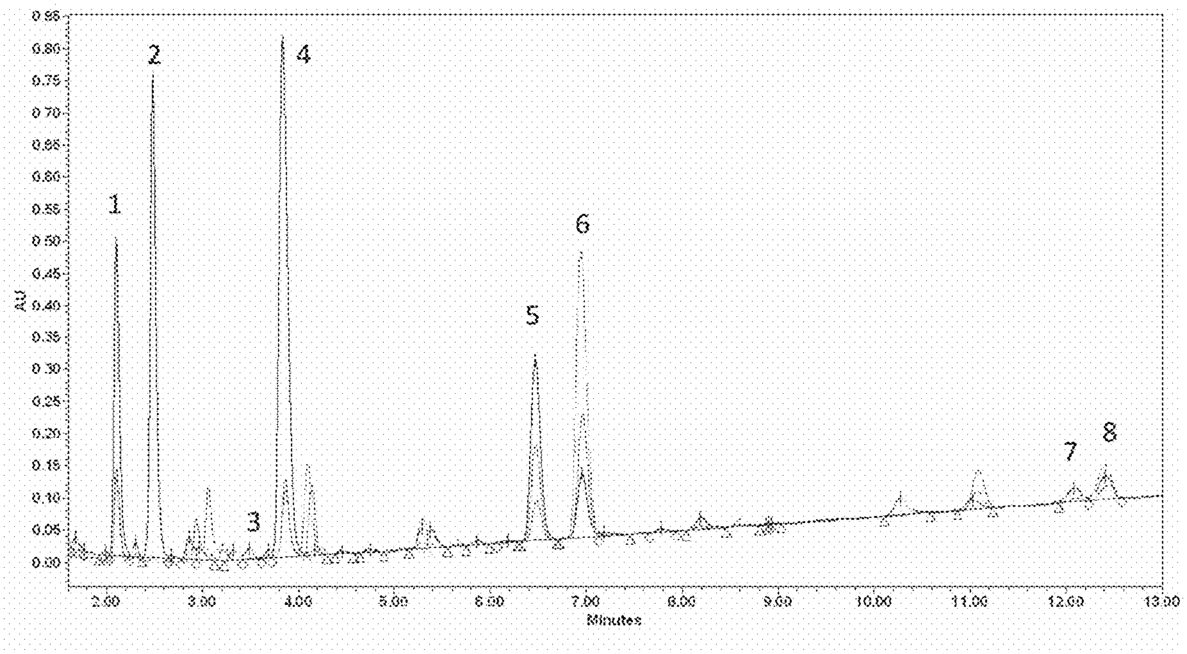
FIG. 1 gives the chromatographic profiles recorded at 200 nm of three pentacyclic triterpene compositions respectively obtained from callus of *Malus* x *domestica* "Cox's Orange Pippin" cultivar, *Malus* x *domestica* "Spartan" cultivar and *Malus* x *domestica* "Golden Delicious" cultivar according to the method of the invention.

Example 1: Preparation of a (poly)hydroxylated pentacyclic triterpenes Composition According to the Method of the Invention In this example, a (poly)hydroxylated pentacyclic triterpenes compositions including 3-O-trans-p-coumaroyl ester of tormentic acid and 3-O-cis-p-coumaroyl ester of tormentic acid and other triterpene compounds has been produced from three different calli of *Malus* x *domestica* cultivars: "Cox's Orange Pippin", "Spartan" and "Golden Delicious". These compositions have further been fractionated to isolate the different pentacyclic triterpenes comprised therein.

1) Materials and Method 1.1. Preparation of the Suspension-Culture Cell Line The callus of the apple cultivar (*Malus* x *domestica* "Cox's Orange Pippin", "Spartan" and "Golden Delicious") were obtained from the Leibniz Institute DSMW (Germany). The calli were cultured on solid fresh Linsmaier and Skoog medium in the dark and subcultured monthly. Cell suspensions were established by resuspending 2-cm callus pieces in liquid Linsmaier and Skoog medium, and subculturing weekly by transferring 30-90% (v/v) of the culture into 50 mL fresh liquid Linsmaier and Skoog medium and incubating at 23° C., with an orbital shaking speed of 140 rpm. Once the cell suspension culture was established, the cells were further subcultured at 15-d intervals by transferring 50% (v/v) into fresh liquid Linsmaier and Skoog medium.

1.2. Elicitation

Methyl jasmonate (Sigma Aldrich 392707-25ML) at 50 µM was added 7-days after sub-subculturing. Cells were harvested after 8-days of incubation at 23° C.

1.3. Extraction of (Poly)Hydroxylated Pentacyclic Triterpenes 50 mL of the suspension cells obtained hereabove at the end of step 1.2. were mixed with 200 mL of ethanol, homogenized, sonicated (37 kHz, 1200 W) for 10 min and shaken for 4 h at 4° C. Samples were then vacuum filtered and stored at 4° C. until fractionation.

1.4. Fractionation

A 5 g C18 Isolute® Solid-Phase Extraction (SPE) cartridge (Biotage, Sweden) was conditioned with 10 mL of ethanol (EtOH), then 10 mL of 1:1 EtOH/$H_2O$ (v:v), and then 10 mL of 25:75 EtOH/$H_2O$ (v:v). Each of the three extracts obtained hereabove at the end of step 1.3. (250 mL) ("Cox's Orange Pippin", "Spartan" and "Golden Delicious" respectively) was coated onto 5 g C18 (silica gel) by rotary evaporation at 40° C. and applied to the preconditioned SPE cartridge. This was eluted with 2×10 mL each of 25:75 EtOH/$H_2O$ (v:v) (Fractions (F) 1 and 2), 50:50 EtOH/$H_2O$ (v:v) (F3-F4), 65:35 EtOH/$H_2O$ (v:v) (F5-F6), 75:25 EtOH/$H_2O$ (v:v) (F7-F8), and 85:15 EtOH/$H_2O$ (v:v) (F9-F10), and 100:0 EtOH/$H_2O$ (v:v) (F11-F12).

1.5. Triterpene Identification and Quantification

For each extract, F7, F8, and F9 contained all triterpenes.

The different fractions F7-F9 obtained hereabove at step 1.4 for each of the three extracts were compared at 200 nm with a Waters Acquity UPLC (Ultra-Performance Liquid Chromatography) system (Milford, MA, USA) hyphenated to a Diode Array Detector (UPLC-DAD). The separation of the 5 µL aliquot was performed on a reverse-phase Acquity UPLC BEH C18 column (2.1×100 mm, 1.7 µm particle size, Waters, Milford, MA, USA). The eluents were 0.05% o-phosphoric acid in water (A) and 0.05% o-phosphoric acid in methanol (B). The gradient was as follows: 0 min, 75% B; 2 min, 75% B; 16 min, 82% B; 25 min, 100% B; 26.5 min, 100% B; 27 min, 75% B; 30 min, 75% B. The flow rate was of 0.3 mL $min^{-1}$ and the column temperature was 40° C. For identification, a high-resolution time of flight mass spectrometer (HR-MS) (TripleTOF 5600+, AB Sciex, Concord, Ontario, Canada) was used.

2) Results

For each extract, F7, F8, and F9 contained all triterpenes.

The chromatographic profiles of the pentacyclic triterpene compositions thus obtained for each of the three fractionated extracts are reported on FIG. 1 annexed. On this figure, intensity of the peaks (in arbitrary units: AU) is expressed as a function of times (in minutes). On this figure, the dotted line corresponds to the profile of the triterpene composition obtained starting from the *Malus* x *domestica* "Cox's Orange Pippin" callus, the full line corresponds to the profile of the triterpene composition obtained starting from the *Malus* x *domestica* "Spartan" callus, and the dashed line corresponds to the profile of the triterpene composition obtained starting from the *Malus* x *domestica* "Golden Delicious" callus. All three triterpene compositions included tormentic acid (peak 1), annurcoic acid (peak 2), 3-O-cis-p-coumaroyltormentic acid (peak 3 (cis)), 3-O-trans-p-coumaroyltormentic acid (peak 4 (trans)), maslinic acid (peak 5), corosolic acid (peak 6), oleanolic acid (7), and ursolic acid (8).

It emerges from these profiles that 3-O-trans-p-coumaroyltormentic acid is the major constituent of the three (poly)hydroxylated pentacyclic triterpene compositions thus obtained. It can also be noted, that the fractions obtained from the callus of *Malus* x *domestica* "Cox's Orange Pippin" cultivar have the highest quantity of (poly)hydroxylated pentacyclic triterpenes and coumaroyl derivatives.

The quantitative composition of the (poly)hydroxylated pentacyclic triterpene mixture present in the fractions obtained from the callus of *Malus* x *domestica* "Cox's Orange Pippin" cultivar is given in Table 1 below:

TABLE 1

| TRITERPENES | Amount (weight %) |
|---|---|
| 3-O-trans-p-coumaroyltormentic acid | 26 |
| 3-O-cis-p-coumaroyltormentic acid | 4 |
| Tormentic acid | 20 |
| Maslinic acid | 16 |
| Annurcoic acid | 12 |
| Corosolic acid | 9 |
| Other triterpenes | 13 |

Example 2: Up-Scaled Preparation of a (Poly)Hydroxylated Pentacyclic Triterpenes Composition According to the Method of the Invention In this example, the culture of the "Cox's Orange Pippin" cell line described in example 1 paragraph 1.1. was further up-scaled in a lab scale bioreactor instrument.

1) Materials and Method 1.1. Environmental Parameters Set for the Cell Suspension Culture in Bioreactor A 4 L bioreactor instrument with flat bottom vessel (Infors HT—minifors 2) and equipped with two 5 cm-diameter impellers adjusted at 0 and 16 cm from the bottom end of the stirring bar was used for the present example. The cell line was inoculated at 20% (v/v) into the reactor filled with a Linsmaier and Skoog medium supplemented with 30 g/L sucrose, 0.2 mg/L of 1-naphtaleneacetic acid and 0.2 mg/L 2,4-dichlorophenoxyacetic acid. The stirring speed was at 150 rpm (revolutions per minute) to prevent (i) any deposition of the cell aggregates at the bottom of the vessel and (ii) an excessive shearing stress. The oxygenation of the medium was supported by an air sparging system set at 0.125 v.v.m. (Vessel Volume per minute). Using these environmental conditions, the kLa (liquid phase mass transfer coefficient) measured in the medium without cells at 23° C. was equal to 0.0735 $min^{-1}$. The batch was run for three weeks to reach to stationary phase.

1.2. Elicitation

Methyl jasmonate (Sigma Aldrich 392707-25ML) was added at the beginning of the stationary phase to reach a final concentration of 50 μM. Cells were harvested after 8-days of incubation at 23° C. Cells were separated from the medium using vacuum filtration, flash frozen in liquid nitrogen and freeze-dried.

1.3. Extraction of (Poly)Hydroxylated Pentacyclic Triterpenes

The total dried cells material (65 g) obtained at the end of step 1.2 was added to 10 L ethanol using a custom-made pilot scale Pignat Solid-liquid extraction system. The mixture was sonicated (37 kHz, 1200 W) for 10 min followed by a mixing step of 2 h at room temperature. The extract was collected and evaporated using a Büchi R-300 rotavapor and re-suspended in 100% EtOH solution.

1.4. Triterpene Purification

The sample extract obtained after step 1.3 was preconditioned using 5 g C18 (Aldrich octadecyl-functionalized silica gel). The triterpene extract was purified using a Reveleris flash chromatography system and a 12 g Reveleris C18 column (Büchi) using a solid type injection, a 30 mL/min flow rate and 5 min cartridge equilibration. Pentacyclic triterpenes were detected using UV wavelength set at 220 nm and 240 nm. A gradient table was set as followed: step 1: time 0 min-65% EtOH, step 2: time 8 min-75% EtOH. Fractions were collected from step2 and were further analyzed as described in example 1 paragraph 1.5.

2) Results

The quantitative composition of the (poly)hydroxylated pentacyclic triterpene composition of the fractions obtained from the callus of *Malus* x *domestica* "Cox's Orange Pippin" cultivar is given in Table 2 below:

TABLE 2

| TRITERPENES | Amount (weight %) |
|---|---|
| 3-O-trans-p-coumaroyltormentic acid | 16 |
| 3-O-cis-p-coumaroyltormentic acid | 5 |
| Tormentic acid | 11 |
| Maslinic acid | 21 |
| Annurcoic acid | 31 |

TABLE 2-continued

| TRITERPENES | Amount (weight %) |
|---|---|
| Corosolic acid | 12 |
| Other triterpenes | 4 |

Example 3: In Vitro Anti-Trypanosomal Activity of 3-O-cis/trans-p-coumaroyltormentic Acid in Comparison to Different Pentacyclic Triterpene Compounds In this example, the in vitro antiparasitic activity of 3-O-trans-p-coumaroyltormentic acid isolated from the fractions obtained at the end of step 1.4 of example 1 with the callus of *Malus* x *domestica* "Cox's Orange Pippin" cultivar, was compared to that of suramine, a commercial anti-trypanosomal drug and to different pentacyclic triterpene compounds.

1) Materials and Method 1.1. Isolation and Identification

For isolation, the different fractions F7-F9 obtained hereabove at step 1.4 of example 1 with the callus of *Malus* x *domestica* "Cox's Orange Pippin" cultivar, were submitted to preparative High Pressure Liquid Chromatography (HPLC) consisting of a Shimadzu® LC-20AP pump hyphenated with a Spd-20AV UV detector. The column used was a Phenomenex Luna® C18, 250×30 $mm^2$ packed with 5 μm particles. The flow rate was 42 mL/min of acetonitrile/methanol/water 45:35:20 (v:v:v). Ten peaks were collected using a detection at 210 nm and 310 nm. A Liquid Chromatography (LC) system consisting in a Thermo Accela pump, autosampler, coupled with a photodiode array UV detector (PAD) and a Thermo Scientific LTQ orbitrap XL mass spectrometer (MS) LC-PAD-MS was used to verify the purity of isolated peaks. The column used was a Phenomenex Luna® C18, 250×4.6 $mm^2$ packed with 5 μm particles. The flow rate was 1 mL/min using an isocratic binary solvent system: solvent A (20%), $H_2O$ pH=6 ($CH_3COONH_4$ 0.02M); solvent B (80%), ACN/MeOH 40:35. Peaks were detected at 210 nm. High-resolution MS was measured with APCI source in the negative mode. The following inlet conditions were applied: capillary temperature 250° C., APCI vaporizer temperature 400° C., sheath gas flow 20.00 u.a., auxiliary gas flow 5.00 u.a., sweep gas flow 5.00 u.a. Data acquisition and processing were performed with Xcalibur software.

1.2. Parasites, Cells and Media

Antiparasitic activities were evaluated in vitro on *Trypanosoma brucei brucei* bloodstream forms (strain 427) (Tbb BSF). Tbb BSF were cultured in vitro at 37° C. with 5% $CO_2$ in HMI9 medium containing 10% heat-inactivated fetal bovine serum, 3-mercaptoethanol (20 mM) and L-cysteine (150 mM).

The cytotoxicity of tested compounds was evaluated in parallel on a Human normal fibroblast cell line (WI-38) cultivated in a humidified atmosphere with 5% $CO_2$ at 37° C. Human normal fibroblast cell line (WI-38) was cultivated in DMEM medium (Life Technologies) containing 4 mM L-glutamine, 1 mM sodium pyruvate supplemented with 10% fetal bovine serum (Sigma) and penicillin-streptomycin (100 UI/mL).

1.3. In Vitro Activity

In vitro tests were performed as previously described by Hoet S. et al. (Planta Med., 2004, 70, 407-413, doi:10.1055/s-2004-818967). Suramine (a commercial anti-trypanosomal drug) and camptothecin were used as positive controls. Stock solutions of compounds to be tested were prepared at a concentration of 10 mg/mL in DMSO. The solutions were further diluted in medium (described in 1.1) to give 0.1 mg/mL stock solutions. Extracts and compounds were tested in eight serial three-fold dilutions (final concentration range: 50-0.02 mg/L) in 96-well microliter plates. All tests were performed at least in duplicate.

2) Results

The anti-trypanosomal activity and toxicity of tested compounds and extracts are reported in Table 3 below:

TABLE 3

| | WI38 ($IC_{50}$ µg/mL) | WI38 ($IC_{50}$ µM) | Tbb ($IC_{50}$ µg/mL) | Tbb ($IC_{50}$ µM) | SI |
|---|---|---|---|---|---|
| Whole fractions F7-F9 of example 1 | 80.40 ± 5.56 | — | 0.87 ± 0.32 | — | 92.4 |
| Tormentic acid | 26.48 ± 0.33 | 54.22 ± 0.67 | 7.49 ± 0.33 | 15.33 ± 0.67 | 3.5 |
| 3-O-cis/trans-p-coumaroyl-tormentic acid | 28.43 ± 0.79 | 44.81 ± 1.25 | 0.48 ± 0.36 | 0.75 ± 0.57 | 59.2 |
| Maslinic acid | 20.85 ± 3.97 | 44.11 ± 8.4 | 4.45 ± 0.64 | 9.41 ± 1.35 | 4.6 |
| Corosolic Acid | 9.34 ± 2.47 | 19.82 ± 5.22 | 3.45 ± 0.23 | 7.30 ± 0.59 | 2.7 |
| Annurcoic acid | 70.17 ± 6.82 | 144.10 ± 14.01 | 27.39 ± 2.24 | 56.29 ± 4.60 | 2.6 |
| Ursolic acid | 5.08 ± 0.10 | 11.14 ± 0.22 | 1.08 ± 0.11 | 2.38 ± 0.24 | 4.8 |
| Oleanolic acid | 28.89 ± 0.34 | 63.26 ± 0.74 | 2.66 ± 0.32 | 5.83 ± 0.70 | 10.9 |
| Camptothecin | 0.04 ± 0.01 | 0.12 ± 0.03 | — | — | — |
| Suramine | — | — | 0.05 ± 0.01 | 0.038 ± 0.008 | — |

In 2005, Pink et al. (Nat Rev Drug Discov, 2005, 4, 727-740, doi:10.1038/nrd1824) published in "Nature Reviews", criteria to select a pure compound as a hit for the treatment of parasitic diseases: this compound has to be active in vitro against whole protozoa with a IC50≤1 mg/L as well as to be selective (being at least tenfold more active against parasite than against a mammalian cell line). Our results show that the whole fraction F7-F9 of example 1 has a significant antitrypanosomal activity (IC50≤1 mg/L) with a high selectivity index, which could be due to its high content in 3-O-cis/trans-p-coumaroyltormentic acid, the only pure compound which could be considered as a hit antitrypanosomal compound ($IC_{50}$1; SI>10).

Example 4: In Vivo anti-trypanosomal Activity of 3-O-cis/trans-p-coumaroyltormentic Acid in Mice In this example, the anti-trypanosomal activity of 3-O-cis/trans-p-coumaroyltormentic acid was tested in vivo in mice in comparison with ursolic acid.

1) Materials and Method 1.1. Animals

NMRI mice (6-8 weeks of age) obtained from Envigo Laboratories (The Netherlands) were used. All in vivo experiments performed were approved by the Ethical Committee for animals use at the Health Sciences Sector of the Catholic University of Louvain (2017/UCL/MD/017).

1.2. In Vivo Acute Toxicity Test

The assessment of the highest tolerated dose was based on a DNDi protocol by Loset J.-R. et al. (V. Drug Screening for Kinetoplastids Diseases. A Training Manual for Screening in Neglected Diseases-DNDi, 2009) and adapted by Beaufay C. et al. (Malar J., 2017, 16, doi:10.1186/s12936-017-2054-y). Briefly, 3-O-cis/trans-p-coumaroyltormentic acid isolated from fractions F-F9 obtained from a callus of *Malus domestica* Cox cultivar of example 1 above was given intraperitoneally every 2 hours to 2 mice using increasing doses: 10-15-25-50 mg/kg from stock solutions of 10 mg/mL. Mice were controlled for any health problem symptoms or behavioral changes and monitored for weight and hematocrit after each injection and every day during 48 h after administration. Main organs (heart, liver, spleen, lung and kidney) of treated mice were observed and weighed wet during autopsy. Control group received the vehicle, distilled water with 10% of tween 80-ethanol (7:3). The total injected dose was finally recorded and will ensure the non-toxicity of in vivo anti-trypanosomal test.

1.3. In Vivo Anti-Trypanosomal Activity

Mice were randomly divided into 6 mice per group for 3-O-cis/trans-p-coumaroyltormentic acid (mixture of cis and trans) and ursolic acid, 4 for positive control (Suramine) and 7 for the negative control, and were infested intraperitoneally with $10^4$ *Trypanosoma brucei brucei*. All compounds were solubilized in the vehicle (water-tween 80-ethanol) and administered intraperitoneally. 3-O-cis/trans-p-coumaroyltormentic acid or ursolic acid (UA) were administered at 50 mg/kg at day 3 after infection with the parasite and then every day until day 7 post-infection. Suramine (0.5 mg/kg) was administered while vehicle was used as a negative control. From day 3 post infection, a drop of blood collected each day from mouse-tail was used to count parasitemia.

2) Results 2.1. In Vivo Acute Toxicity

The results show that no acute toxic symptom was observed in each group (UA and 3-O-cis/trans-p-coumaroyltormentic acid) after the repeated injections of the treatments which did not impact neither weights nor haematocrits. As autopsy of treated mice did not reveal any macroscopic signs of toxicity and organs weights were normal, the total cumulative highest tolerated doses were evaluated as 100 mg/kg for both compounds.

2.2. In Vivo Anti-Trypanosomal Activity

Figure 2:
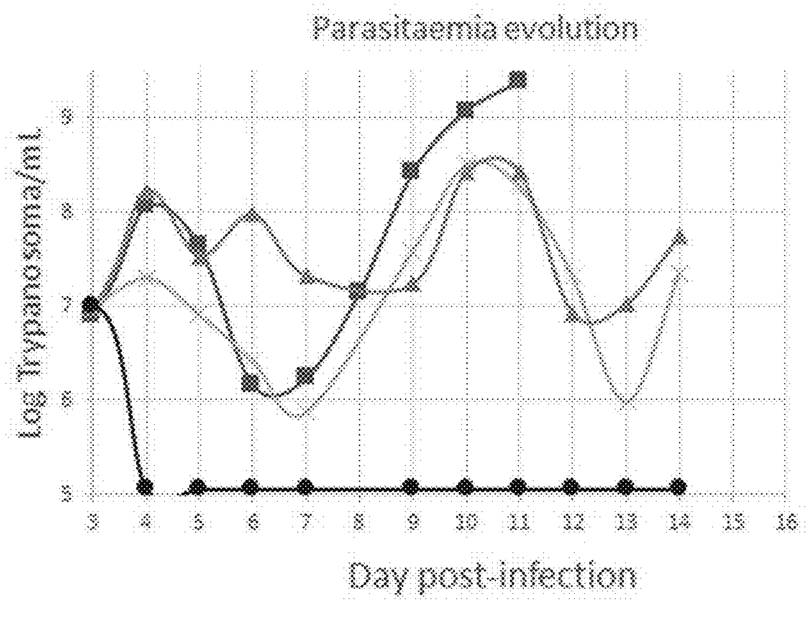
FIG. 2 reports the evolution of parasitemia (Log *Trypanosoma*/mL) as a function of time (in days) in mice infested intraperitoneally with $10^4$ *Trypanosoma brucei* and treated intraperitoneally by 3-O-cis/trans-p-coumaroyltormentic acid or ursolic acid (UA) at 50 mg/kg at day 3 after infection with the parasite and then every day until day 7 post-infection. Positive control: suramine (0.5 mg/kg)
Figure 3:
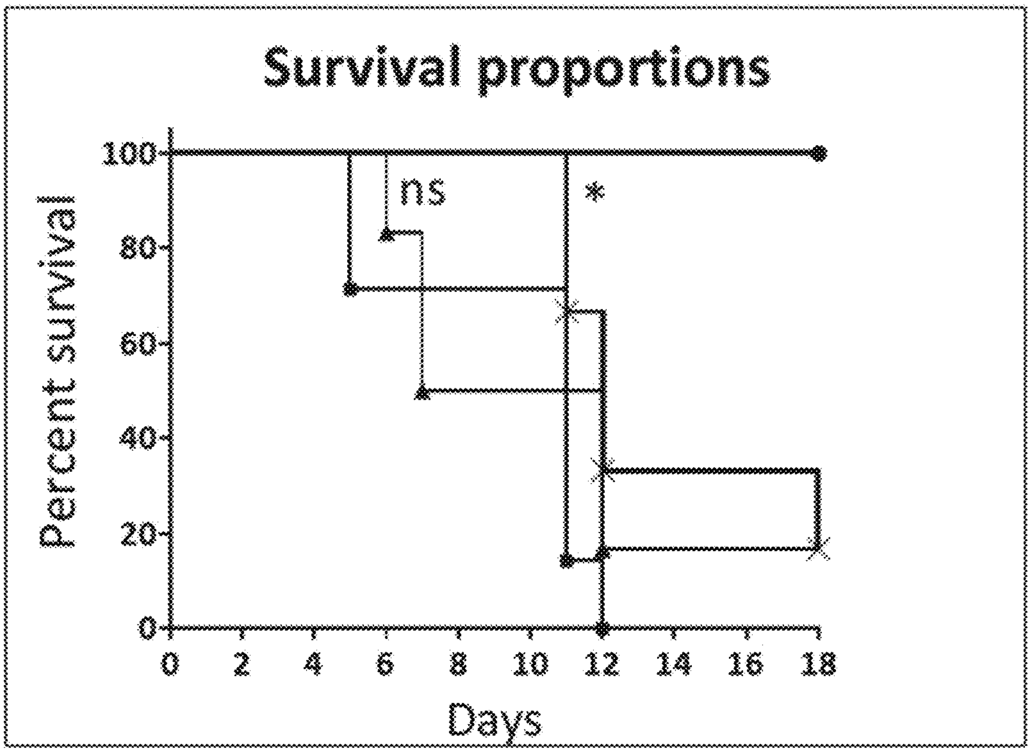
FIG. 3 reports the results of mice survival. On this figure, the percentage of survivals in given as a function of time (in days). The values with full squares correspond to the negative control, the values with crosses correspond to mice administered with 3-O-cis/trans-p-coumaroyltormentic acid, the values with full triangles correspond to mice administered with ursolic acid and the values with full dots correspond to the positive control, i.e. to mice administered with suramine.

The results are reported on FIGS. 2 and 3 annexed.

FIG. 2 reports the results of the antitrypanosomal activity in vivo. On this figure, parasitemia (Log *Trypanosoma*/mL) is given as a function of time (in days). The curve with full squares corresponds to the negative control, the curve with crosses corresponds to 3-O-cis/trans-p-coumaroyltormentic acid, the curve with full triangles corresponds to ursolic acid and the curve with full dots corresponds to the positive control (Suramine).

FIG. 3 reports the results of survival. On this figure, the percentage of survivals in given as a function of time (in days). The values with full squares correspond to the negative control, the values with crosses correspond to 3-O-cis/trans-p-coumaroyltormentic acid, the values with full triangles correspond to ursolic acid and the values with full dots correspond to the positive control (Suramine).

The results presented on FIG. 2 show that the mixture of 3-O-cis/trans-p-coumaroyltormentic acids exhibit a significant decrease of the parasitemia on day 4 post-infection when administered intraperitoneally at 50 mg/kg/day. This compound was more active than UA which did not show any effect on the parasitemia count.

Concerning survival analyses (FIG. 3), the esters treatment significantly improved the survival of infected mice in comparison to the untreated group, contrarily to UA for which no significant difference was observed at day 19 post-infection. Positive control mice survive during all the experimental period while all mice died after 12 days in the negative control group and in both treated groups only one mouse survived till the end of the experiment. Remaining mice were euthanized on day 19 post-infection. Of note, on day 12 post-infection, survival increases of 16.7% and 33.3% were observed for UA and esters treated mice respectively.

Example 5: Synthesis of Derivatives of Formulae (II-1) to (II-1)

Derivatives of formulae (II-1) to (II-10) were synthetized starting from oleanolic acid and ursolic acid present in the fractions obtained according to example 1 above.

Hydroxyl function at position 3 from the oleanolic and ursolic acids template was targeted to synthetize cinnamic esters following the Steglich esterification. The triterpenic acid (1.3 equivalents) was treated with dicyclohexylcarbodiimide (DCC: 2.2 equivalents) and 4-dimethylaminopyridine as a catalyst (DMAP: 0.2 equivalent) in toluene at 80° C. under agitation and argon or nitrogen gas as described by Lee et al. (Planta Med., 2008, 74 (12), 1481-1487). Aromatic acids reagents: cinnamic and hydrocinnamic acids or some fluorophenylpropionic acid isomers (ortho/meta/para) were firstly incubated during two hours with DMAP to ensure carboxylic function activation. After filtration, a purification was performed on a silica gel column (Merck, silica gel 60, 0.065-2 mm) with a toluene-ethyl acetate gradient. When necessary, an additional purification step by semi-preparative HPLC was performed with a Phenomenex Luna C18 (2) column (250×10 $mm^2$ with 5 μm as particle size) on a Shimadzu Prominence system (LC20-AP pumps and SPD-20AV UV/VIS detector) with 100% methanol at 3 mL/min. The purity was checked at 210 nm with the analytical column (250×4.6 $mm^2$), a flow rate of 1 mL/min and a binary solvent system composed with acetonitrile and Milli-Q water as followed: 50% acetonitrile 0-2 min, 100% acetonitrile 27-42 min, 50% acetonitrile 43-50 min.

The derivative of formula (II-1), named 3-O-hydrocinnamic ursolic acid ($C_{39}H_{56}O_4$) was obtained with a yield of 51.8% and a purity >95%.

HRMS (APCI): m/z=587.41 (M−$H^+$) (587.40949 calculated for $C_{39}H_{55}O_4$), 437.34 ($C_{30}H_{45}O_2$=M−$H^+$—$C_9H_{10}O_2$); $^1$H NMR (400 MHz, $CDCl_3$) δ 7.28-7.25 (m, 2H, H-2'/-4'), 7.20 (d, J=7.6 Hz, 3H, H-1'/-3'/-5'), 5.23 (d, J=3.6 Hz, 1H, H-12), 4.50 (dd, J=9.7, 6.2 Hz, 1H, H-3), 2.95 (t, J=7.8 Hz, 2H, H-7'), 2.63 (ddd, J=9.0, 6.8, 1.5 Hz, 2H, H-8'), 2.17 (d, J=11.3 Hz, 1H, H-18), 2.1-0 (m, 43H).

The derivative of formula (II-2), named 3-O-cinnamic ursolic acid ($C_{39}H_{54}O_4$) was obtained with a yield of 17.6%) and a purity >95%.

HRMS (APCI): m/z=585.39 (M−$H^+$), 437.34 ($C_{30}H_{45}O_2$=M−$H^+$—$C_9H_8O_2$); $^1$H NMR (400 MHz, $CDCl_3$) δ 7.67 (d, J=16.0 Hz, 1H, H-7'), 7.53-7.38 (m, 5H, H1'-5' aromatic), 6.45 (d, J=16.0 Hz, 1H, H-8'), 5.26 (d, J=3.5 Hz, 1H, H-12), 4.65 (t, J=8.1 Hz, 1H, H-3), 2.19 (d, J=11.2 Hz, 1H, H-18), 2.08-0.75 (m, 43H).

The derivative of formula (II-3), named 3-O-parafluorophenylpropionic ursolic acid ($C_{39}H_{55}O_4F$) was obtained with a yield of 5.8% and a purity >95%.

HRMS (APCI): m/z=605.40027 (M−$H^+$) (605.40006 calculated for $C_{39}H_{54}O_4F$), 437.34 ($C_{30}H_{45}O_2$=M−$H^+$—$C_9H_9O_2F$); $^1$H NMR (400 MHz, $CDCl_3$) δ 7.16 (m, 2H, H-17-5'), 6.96 (m, 2H, H-2'/-4'), 5.23 (t, J=3.4 Hz, 1H, H-12), 4.50 (dd, J=8.0, 6.9 Hz, 1H, H-3), 2.93 (t, J=7.6 Hz, 2H, H-7'), 2.69-2.53 (m, 2H, H-8'), 2.18 (d, J=11.1 Hz, 1H, H-18), 2.10-0.60 (m, 43H).

The derivative of formula (II-4), named 3-O-metafluorophenylpropionic ursolic acid ($C_{39}H_{55}O_4F$) was obtained with a yield of 7.9% and a purity >95%.

HRMS (APCI): m/z=605.40 (M−$H^+$) (605.40006 calculated for $C_{39}H_{54}O_4F$), 437.34 ($C_{30}H_{45}O_2$=M−$H^+$—$C_9H_9O_2F$); $^1$H NMR (400 MHz, $CDCl_3$) δ 7.22 (dd, J=8.0, 6.1 Hz, 1H, H-2'), 6.98-6.85 (m, 3H, H-1'/-3'/-5'), 5.25 (t, J=3.6 Hz, 1H, H-12), 4.53-4.45 (m, 1H, H-3), 2.95 (t, J=7.7 Hz, 2H, H-7'), 2.63 (dd, J=8.4, 6.9 Hz, 2H, H-8'), 2.18 (d, J=11.2 Hz, 1H, H-18), 2.08-0.70 (m, 43H).

Derivative of formula (II-5), named 3-O-orthofluorophenylpropionic ursolic acid ($C_{39}H_{55}O_4F$) was obtained with a yield of 51.7% and a purity >95%.

HRMS (APCI): m/z=605.40 (M−$H^+$) (605.40006 calculated for $C_{39}H_{54}O_4F$), 437.34 ($C_{30}H_{45}O_2$=M−$H^+$—$C_9H_9O_2F$); $^1$H NMR (400 MHz, $CDCl_3$) δ 7.24-7.13 (m, 2H, H-17-5'), 7.07-6.97 (m, 2H, H-27-4'), 5.23 (t, J=3.5 Hz, 1H, H-12), 4.55-4.42 (m, 1H, H-3), 2.98 (t, J=7.8 Hz, 2H, H-7'), 2.64 (dd, J=8.5, 7.1 Hz, 2H, H-8'), 2.18 (d, J=11.2 Hz, 1H, H-18), 1.99-0.70 (m, 43H).

Derivative of formula (II-6), named 3-O-hydrocinnamic oleanolic acid ($C_{39}H_{56}O_4$) was obtained in the form of an amorphous white powder with a yield of 5.2% and a purity >95%.

HRMS (APCI): m/z=587.53970 (M−$H^+$) (587.40949 calculated for $C_{39}H_{55}O_4$), 437.45272 ($C_{30}H_{45}O_2$=M−$H^+$—$C_9H_{10}O_2$) and m/z=589.42331 (M+$H^+$) (587.40949 calculated for $C_{39}H_{57}O_4$), 439.35543 ($C_{30}H_{47}O_2$=M+$H^+$—$C_9H_{10}O_2$, major one), 393.35082 ($C_{29}H_{45}$=M+$H^+$—$C_9H_{10}O_2$—$CH_2O_2$); $^1$H-NMR (400 MHz, $CDCl_3$): δ=7.28-7.01 (m, 5H, H1'-5' aromatic), 5.20 (d, J=3.5 Hz, 1H, H-12), 4.42 (dd, J=10.2, 5.7 Hz, 1H, H-3), 2.88 (t, J=7.8 Hz, 2H, H-7'), 2.75 (dd, J=13.9, 4.5 Hz, 1H, H-18), 2.56 (dd, J=8.9, 6.7 Hz, 2H, H-8'), 2.00-0.51 (m, 43H).

Derivative of formula (II-7), named 3-O-cinnamic oleanolic acid ($C_{39}H_{54}O_4$) was obtained in the form of a yellow powder with a yield of 21.8% and a purity >95%.

HRMS (APCI): m/z=585.39478 (M−$H^+$) (585.39384 calculated for $C_{39}H_{53}O_4$), 437.34171 ($C_{30}H_{45}O_2$=M−$H^+$—$C_9H_8O_2$) and m/z=587.39413 (M+$H^+$) (587.40949 calculated for $C_{39}H_{55}O_4$), 439.35565 ($C_{30}H_{47}O_2$=M+$H^+$—$C_9H_8O_2$, major one), 391.28323 ($C_{29}H_{43}$=M+$H^+$—$C_9H_8O_2$—$CH_4O_2$); $^1$H-NMR (400 MHz, $CDCl_3$): δ=7.68 (d, J=16.0 Hz, 1H, H-7'), 7.50-7.41 (m, 5H, H-1'-5' aromatic), 6.45 (d, J=16.0 Hz, 1H, H-8'), 5.27 (d, J=3.5 Hz, 1H, H-12), 4.49 (m, 1H, H-3), 2.8 (dd, J=13.8, 4.5 Hz, 1H, H-18), 2.03-0.65 (m, 43H).

Derivative of formula (II-8), named 3-O-parafluorophenylpropionic oleanolic acid ($C_{39}H_{55}O_4F$) was obtained in the form of white crystals with a yield of 13.0% and a purity >95%.

HRMS (APCI): m/z=605.40161 ($M-H^+$) (605.40006 calculated for $C_{39}H_{54}O_4F$), 437.34286 ($C_{30}H_{45}O_2$=$M-H^+$—$C_9H_9O_2F$) and m/z=607.41408 ($M+H^+$) (607.41571 calculated for $C_{39}H_{56}O_4F$), 439.35565 ($C_{30}H_{47}O_2$=$M+H^+$—$C_9H_9O_2F$, major one), 393.35065 ($C_{29}H_{45}$=$M+H^+$—$C_9H_9O_2F$—$CH_2O_2$); $^1$H-NMR (400 MHz, $CDCl_3$): δ=7.19-7.11 (m, 2H, H-1'-5'), 7.00-6.90 (m, 2H, H-2'/-4'), 5.26 (t, J=3.6 Hz, 1H, H-12), 4.55-4.41 (m, 1H, H-3), 2.92 (t, J=7.3 Hz, 2H, H-7'), 2.82 (dd, J=13.8, 4.5 Hz, 1H, H-18), 2.60 (dd, J=8.5, 6.8 Hz, 2H, H-8'), 2.01-0.67 (m, 43H).

Derivative of formula (II-9), named 3-O-metafluorophenylpropionic oleanolic acid ($C_{39}H_{55}O_4F$) was obtained in the form of a yellow solid with a yield of 36.8% and a purity >95%.

HRMS (APCI): m/z=605.51654 ($M-H^+$) (605.40006 calculated for $C_{39}H_{54}O_4F$), 437.51715 ($C_{30}H_{45}O_2$=$M-H^+$—$C_9H_9O_2F$) and m/z=607.41416 ($M+H^+$) (607.41571 calculated for $C_{39}H_{56}O_4F$), 439.35569 ($C_{30}H_{47}O_2$=$M+H^+$—$C_9H_9O_2F$, major one), 393.35102 ($C_{29}H_{45}$=$M+H^+$—$C_9H_9O_2F$—$CH_2O_2$); $^1$H-NMR (400 MHz, $CDCl_3$): δ=7.40-7.08 (m, 1H, H-2'), 7.06-6.80 (m, 3H, H-1'/-3'/-5'), 5.27 (d, J=3.5 Hz, 1H, H-12), 4.50 (dd, J=10.0, 6.1 Hz, 1H, H-3), 2.95 (t, J=7.7 Hz, 2H, H-7'), 2.82 (dd, J=13.9, 4.5 Hz, 1H, H-18), 2.63 (t, J=7.7 Hz, 2H, H-8'), 2.12-0.53 (m, 43H).

The derivative of formula (II-10), named 3-O-orthofluorophenylpropionic oleanolic acid ($C_{39}H_{55}O_4F$) was obtained in the form of an amorphous yellow powder with a yield of 1.8% and a purity >95%.

HRMS (APCI): m/z=605.54545 ($M-H^+$) (605.40006 calculated for $C_{39}H_{54}O_4F$), 437.56130 ($C_{30}H_{45}O_2$=$M-H^+$—$C_9H_9O_2F$) and m/z=607.41409 ($M+H^+$) (607.41571 calculated for $C_{39}H_{56}O_4F$), 439.35565 ($C_{30}H_{47}O_2$=$M+H^+$—$C_9H_9O_2F$, major one), 393.35097 ($C_{29}H_{45}$=$M+H^+$—$C_9H_9O_2F$—$CH_2O_2$); $^1$H-NMR (400 MHz, $CDCl_3$): 7.12 (m, 2H, H-1'/-5'), 7.03-6.86 (m, 2H, H-2'/-4'), 5.27-5.13 (m, 1H, H-12), 4.49-4.35 (m, 1H, H-3), 2.91 (t, J=7.9 Hz, 2H, H-7'), 2.75 (dd, J=13.8, 4.5 Hz, 1H, H-18), 2.57 (t, J=7.8 Hz, 2H, H-8'), 2.00-0.58 (m, 43H).

Example 6: Antitrypanosomal Activities of Derivatives of Formula (II-1) to (II-10)

Semi-synthetized derivatives of 3-O-p-coumaroyl tormentic acid of formulae (II-1) to (II-10) were tested for their antitrypanosomal activities and selectivity towards mammalian cells according to the same methods as described above in example 3. The results of the activity and selectivity are given in Table 4 below:

TABLE 4

| DERIVATIVES | Biological activities expressed in $IC_{50}$ (μM, Mean ± Sd) Antitrypanosomal (Tbb) | Cytotoxicity (WI38) | SI ($IC_{50}$WI38/ $IC_{50}$Tbb) |
|---|---|---|---|
| (II-1) | 2.22 ± 0.66 | 142.01 ± 3.45 | 64.0 |
| (II-2) | 68.19 ± 2.15 | nd | nd |
| (II-3) | 2.45 ± 0.30 | >164.90 | >67.3 |
| (II-4) | 2.67 ± 0.83 | >164.90 | >61.5 |
| (II-5) | 1.66 ± 0.38 | >131.92 | >79.5 |
| (II-6) | 2.59 ± 0.87 | 23.54 ± 6.56 | 9.1 |
| (II-7) | 6.31 ± 0.96 | 22.31 ± 1.88 | 3.5 |
| (II-8) | 2.88 ± 1.11 | 16.33 ± 3.26 | 5.7 |
| (II-9) | 1.72 ± 0.07 | 20.74 ± 2.25 | 12.1 |
| (II-10) | 4.63 ± 0.28 | 18.61 ± 4.47 | 4.0 |

Activity of all tested 3-O-ursane esters, except the cinnamic one (derivative of formula (II-2)), was similar to ursolic acid with an enhanced selectivity, especially for aromatic esters (Derivatives of formulae (II-1) and (II-3) to (II-5)). For 3-O-oleanane derivatives, activity also remained similar than oleanolic acid except the hydrocinnamic derivative (derivative of formula (II-6)) and para/meta-fluorophenylpropionic derivatives (derivatives of formulae (II-8) and (II-9)) showing a significantly increased activity but also cytotoxicity leading to similar selectivity.

Example 7: Evaluation of the Triterpene Composition in *Malus* x *domestica* (Rosaceae) and *Vitellaria paradixa* (Sapotaceae)

In this example, the triterpene composition obtained using the *Malus* x *domestica* "Cox's Orange Pippin" cell line described in examples 1 and 2 was compared to those obtained using "Cox's Orange Pippin" apple fruit skin (raw material—example not forming part of the present invention), *Vitellaria paradoxa* leaf (raw material—example not forming part of the present invention) and *Vitellaria paradoxa* calli (cell) samples (obtained according to the process of the present invention).

1) Materials and Method 1.1. Sample Preparation

The "Cox Orange Pippin" cell sample was obtained after a batch culture using a 6 L custom-made stirred-bioreactor instrument with round bottom vessel (Biostream) and equipped with two 8.5 cm-diameter marine impellers adjusted at 0 and 24 cm from the bottom end of the stirring bar. The cell line was inoculated at 13% (v/v) into the reactor filled with a Linsmaier and Skoog medium supplemented with 30 g/L sucrose, 6 mg/L of 1-naphtaleneacetic acid. The stirring speed was at 105 rpm (revolutions per minute). The oxygenation of the medium was supported by an air sparging system set at 0.125 v.v.m. (Vessel Volume per minute) as already described in the example 2. Methyl jasmonate (Sigma Aldrich 392707-25ML) was added at the beginning of the stationary phase to reach a final concentration of 50 μM. Cells were harvested after 8-days of incubation at 23° C. Cells were separated from the medium using vacuum filtration.

*Vitellaria paradoxa* calli culture was initiated and multiplied from leaf explant placed on a Murashige and skoog medium supplied with 30 g agar, 0.2 mg/l 1-naphtaleneacetic acid and 0.2 mg/l 2,4-dichlorophenoxyacetic acid. Calli were obtained after 2 months and were further spitted each month.

*Vitellaria paradoxa* leaf and *Malus* x *domestica* 'Cox Orange pippin' skin samples have to be considered as comparative examples not forming part of the present invention. *Vitellaria paradoxa* leaf samples were collected from a two years-old plant grown in a pot filed with a soil/sand (70/30, v/v) mixture at 30° C. and 60% relative humidity.

Cox Orange Pippin skin samples were obtained from fruits collected in October 2016 and peeled with scalpels.

*Vitellaria paradoxa* leaf and cell (calli) samples as well as *Malus* x *domestica* "Cox Orange pippin" fruit skin and cell samples were collected, directly flash-frozen in liquid nitrogen, freeze-dried and ground.

1.2. Laboratory Scale Wide Spectrum Extraction Procedure

In order to evaluate the triterpene content of these heterogeneous samples, a wide spectrum extraction procedure was used. 10 ml of an ethyl acetate/hexane mixture (50/50, v/v) was added to 500 mg dried samples in a 15 ml Tube. Samples were homogenized using vortex and sonicated for 10 min, and finally shaken at 20 Hz for 20 min in a (mill grinder Retsch). After centrifugation at 4700 g/20 min/20° C., the supernatant was collected and evaporated. The remaining pellet was re-extracted using 10 mL ethanol/water mixture (80/20, v/v), homogenized using vortex and sonicated for 10 min, and finally shaken at 20 Hz for 20 min in a (mill grinder Retsch). After centrifugation at 4700 g/20 min/20° C., the supernatant was combined to the lipophilic dried extract and further evaporated during 7 h. The final extract was re-suspended in 1.5 mL and filtrated on PTFE 0.2 μm. Samples were analyzed as described in example 1 paragraph 1.5.

2) Results

The quantitative composition of the (poly)hydroxylated pentacyclic triterpene composition obtained from *Malus* x *domestica* "Cox's Orange Pippin" cultivar and *Vitellaria paradoxa* samples is given in Table 5 below:

TABLE 5

| | Amount (weight %) | | | |
|---|---|---|---|---|
| TRITERPENES | Cox Orange Pippin cell | Cox orange Pippin fruit skin (1) | *Vitellaria paradoxa* cell | *Vitellaria paradoxa* leaf (1) |
| Tormentic acid | 8.25 | 2.49 | 39.92 | 0.00 |
| Annurcoic acid | 29.28 | 29.67 | 0.00 | 0.00 |
| 3-O-trans-p-coumaroyl tormentic acid | 32.88 | 0.00 | 7.35 | 1.57 |
| 3-O-cis-p-coumaroyl tormentic acid | 1.59 | 0.00 | 0.00 | 0.00 |
| Maslinic acid | 13.69 | 2.76 | 13.02 | 0.00 |
| Corosolic acid | 7.47 | 3.03 | 15.09 | 0.87 |
| Betulin | 0.00 | 1.65 | 0.00 | 0.84 |
| Betulinic acid | 0.00 | 3.15 | 0.00 | 0.00 |
| Oleanolic acid | 1.55 | 15.53 | 4.58 | 11.89 |
| Ursolic acid | 3.50 | 30.85 | 10.20 | 43.70 |
| Betulinaldehyde | 0.00 | 1.32 | 0.00 | 0.00 |
| Oxidosqualene | 0.00 | 0.93 | 14.91 | 4.24 |
| Lupeol | 1.77 | 8.61 | 0.00 | 36.95 |

(1) comparative example not forming part of the present invention

It clearly emerges from these results that the fractions obtained according to the process according to the invention exhibit a very higher amount of 3-O-trans-p-coumaroyl tormentic acid compared to the samples obtained by a simple extraction, for both Cox Orange Pippin and *Vitellaria paradoxa*.

The same applies to the amount of 3-O-cis-p-coumaroyl tormentic acid obtained from Cox Orange Pippin when the process according to the invention is used.

The invention claimed is:

1. A method for producing, from a plant cell suspension culture, a composition comprising a mixture of (poly)hydroxylated pentacyclic triterpenes including at least a 3-O-p-coumaroyl ester of tormentic acid, wherein said method comprises at least the following steps:

1) providing a suspension-cultured cell line capable of producing a mixture of (poly)hydroxylated pentacyclic triterpenes including at least a 3-O-p-coumaroyl ester of tormentic acid, said suspension-cultured cell line being cultured in a liquid culture medium from a callus of a plant selected from the group consisting of Rosaceae and Sapotaceae families;

2) adding in said liquid culture medium at least one elicitor and culturing the suspension-cultured cell line of step 1) in said liquid culture medium during a period of time sufficient to produce said mixture of (poly)hydroxylated pentacyclic triterpenes including at least a 3-O-p-coumaroyl ester of tormentic acid;

3) extracting said mixture of (poly)hydroxylated pentacyclic triterpenes including at least a 3-O-p-coumaroyl ester of tormentic acid and/or a derivative thereof from the liquid culture medium with a solvent, to obtain a first composition comprising said mixture of (poly)hydroxylated pentacyclic triterpenes including a first concentration C1 of a 3-O-p-coumaroyl ester of tormentic acid in said solvent, 4) submitting the first composition of step 3) to a silica gel chromatography to obtain a second composition comprising a mixture of (poly)hydroxylated pentacyclic triterpenes including a second concentration C2 of said 3-O-p-coumaroyl ester of tormentic acid, with C2 being higher than C1, wherein the plant of the group of the Rosaceae family is the species *Malus* x *domestica* and the plant of the group of Sapotaceae is the species *Vitellaria paradoxa*.

2. The method according to claim 1, wherein the callus used to prepare the suspension-cultured cell line of step 1) is obtained from the fruits when the plant belongs to the Rosaceae family or from the leaves when the plant belongs to the Sapotaceae family.

3. The method according to claim 1, wherein the callus used to prepare the suspension-cultured cell line of step 1) is a callus obtained from a fruit of the Rosaceae family.

4. The method according to claim 1, wherein said elicitor is selected from the group consisting of abscisic acid, auxins, brassinosteroids, cytokinins, ethylene, gibberellins, salicylic acid, strigolactones and jasmonates.

5. The method according to claim 1, wherein said elicitor is methyl jasmonate.

6. The method according to claim 1, wherein the liquid culture medium used during step 2) comprises sugar as a carbon source and at least one additional plant hormone in the auxin family.

7. The method according to claim 1, wherein the liquid culture medium during step 2) is a Linsmaier and Skoog medium further comprising sucrose as carbon source, and 1-naphtaleneacetic acid and 2,4-dichlorophenoxyacetic acid as additional plant hormone in the auxin family.

8. The method according to claim 1, wherein step 2) is carried out at a temperature ranging from 20 to 25° C., during a period of time ranging from 1 week to 4 weeks.

9. The method according to claim 1, wherein the solvent used during step 3) is selected from the group consisting of ethyl acetate, hexane, n-butanol, dichloromethane, ethanol, methanol, acetone, and mixtures thereof.

10. The method according to claim 1, wherein the mixture of (poly)hydroxylated pentacyclic triterpenes present in the first composition obtained at the end step 3) comprises 3-O-trans-p-coumaroyltormentic acid and/or 3-O-cis-p-coumaroyltormentic acid and at least one pentacyclic triterpene compound selected from the group consisting of tormentic acid, maslinic acid, annurcoic acid and corosolic acid.

11. The method according to claim 1, wherein at the end of step 4), the second composition comprises a concentration C2 of 3-O-trans-p-coumaroyltormentic acid and/or of 3-O-cis-p-coumaroyltormentic acid of at least 10 weight % with regards to the total weight of the mixture of (poly) hydroxylated pentacyclic triterpenes present in said second composition.

12. The method according to claim 1, wherein when the callus used in step 1) is obtained from a plant of Rosaceae family then the mixture of (poly)hydroxylated pentacyclic triterpenes of the second composition obtained at the end of step 4) comprises from 10 to 33 weight % of 3-O-trans-p-coumaroyltormentic acid, from 1 to 6 weight % of 3-O-cis-p-coumaroyltormentic acid, from 6 to 20 weight % of tormentic acid, from 9 to 21 weight % of maslinic acid, from 7 to 32 weight % of annurcoic acid and from 5 to 12 weight % of corosolic acid with regards to the total weight of the mixture of (poly)hydroxylated pentacyclic triterpenes present in said composition.

13. The method according to claim 12, wherein the second composition obtained at the end of step 4) comprises:

i) 26 weight % of 3-O-trans-p-coumaroyltormentic acid, 4 weight % of 3-O-cis-p-coumaroyltormentic acid, 20 weight % of tormentic acid, 16% weight % of maslinic acid, 12 weight % of annurcoic acid and 9 weight % of corosolic acid, or ii) 16 weight % of 3-O-trans-p-coumaroyltormentic acid, 5 weight % of 3-O-cis-p-coumaroyltormentic acid, 11 weight % of tormentic acid, 21% weight % of maslinic acid, 31 weight % of annurcoic acid and 12 weight % of corosolic acid, or iii) 33 weight % of 3-O-trans-p-coumaroyltormentic acid, 1.5 weight % of 3-O-cis-p-coumaroyltormentic acid, 8 weight % of tormentic acid, 29 weight % of annurcoic acid, 13.5 weight % of maslinic acid, and 7.5 weight % of corosolic acid.

14. The method according to claim 1, wherein said method further comprises an additional step 5) of isolating said 3-O-p-coumaroyl ester of tormentic acid from the second composition obtained at the end of step 4), in order to obtain a third composition containing only 3-O-trans-p-coumaroyltormentic acid and/or 3-O-cis-p-coumaroyltormentic acid.

15. The method according to claim 1, further comprising a step of preparing a derivative of said 3-O-p-coumaroyl ester of tormentic acid and including it in said composition.

16. The method according to claim 15, wherein said derivative of said 3-O-p-coumaroyl ester of tormentic acid is represented by formula (II) below:

(II)

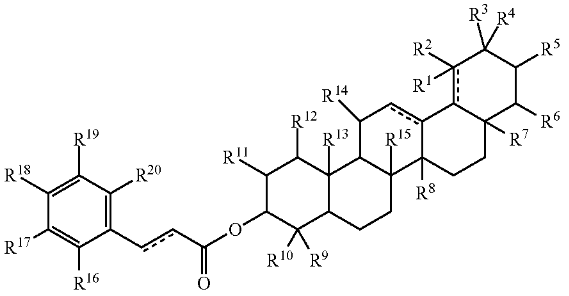

wherein $R^1$ to $R^{15}$ are each individually selected from the group consisting of H, OH, O-alkyl, alkyl, =O, $CH_2OH$, COOH and COO-alkyl;

$R^{16}$ to $R^{20}$, are each individually selected from the group consisting of H, OH, O-alkyl, alkyl, =O, $CH_2OH$, COOH and X, wherein X=F, Cl or Br;

the bond represented by a continuous line doubled with a dotted line corresponds either to a single bond or a double bond.

* * * * *